United States Patent [19]

Baiocchi

[11] 4,154,962
[45] * May 15, 1979

[54] SYNTHESIS OF HYDRATROPIC ACID AND SOME OF ITS ALKYL DERIVATIVES

[75] Inventor: Leandro Baiocchi, Rome, Italy

[73] Assignee: Aziende Chimiche Riunite Angelini Francesco A.C.R.A.F. S.p.A., Rome, Italy

[*] Notice: The portion of the term of this patent subsequent to Jun. 27, 1995, has been disclaimed.

[21] Appl. No.: 847,629

[22] Filed: Nov. 1, 1977

Related U.S. Application Data

[63] Continuation of Ser. No. 627,333, Oct. 30, 1975, abandoned.

[30] Foreign Application Priority Data

Jan. 21, 1975 [IT] Italy .................... 47762 A/75

[51] Int. Cl.² .............................. C07C 63/52
[52] U.S. Cl. ................ 562/496; 260/343.6; 562/508
[58] Field of Search ............ 260/515 R; 562/496

[56] References Cited

U.S. PATENT DOCUMENTS 4,097,522  6/1978  Baiocchi ........................ 260/515

Primary Examiner—Bernard Helfin
Assistant Examiner—G. T. Breitenstein
Attorney, Agent, or Firm—Ladas, Parry, Von Gehr, Goldsmith & Deschamps

[57] ABSTRACT

A new process by which cyclohexanone is treated, in the presence of a suitable acid or a salt of an organic base, with pyruvic acid or with one of its simple derivatives (ester or salt) to give hydratropic acid.

13 Claims, No Drawings

SYNTHESIS OF HYDRATROPIC ACID AND SOME OF ITS ALKYL DERIVATIVES

This is a continuation of application Ser. No. 627,333 filed Oct. 30, 1975, now abandoned.

Through hydratropic acid (Ia) has been known since the past century (W, Wislicenas, Goldstein, 1855) all processes for its synthesis which have been described in literature, start from mono-substituted benzene derivatives

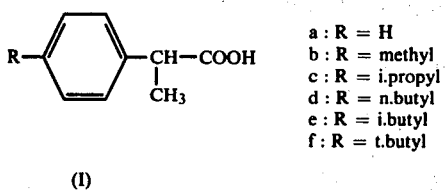

a : R = H
b : R = methyl
c : R = i.propyl
d : R = n.butyl
e : R = i.butyl
f : R = t.butyl (I)

and require the transformation of the side chain through several subsequent steps. The present invention relates to the synthesis of hydratropic acid and of its p. alkyl-substituted analogues starting from cyclohexanone or from 3-alkyl-cyclohexanones (II) and pyruvic acid, according to the following scheme

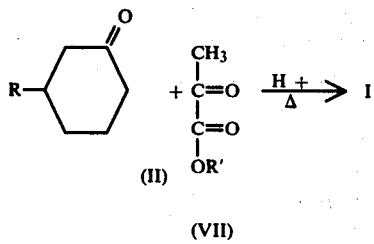

(VII)

Pyruvic acid can be substituted by one of its alkaline or alkaline earth salts (Na, Li, K, Ca) or by one of its esters (R is methyl, ethyl, propyl, butyl) or it can even be produced "in situ" by pyrrolisis of tartaric acid. R could be any alkyl containing 1 to 4 atoms, like methyl, ethyl, propyl, isopropyl, butyl, isobutyl, t.butyl.

The reaction conditions can remarkably change from one case to another. It is therefore possible to divide the reaction in two different steps, first condensing, cyclohexanone and pyruvic acid, and secondly provoking the aromatization of the intermediate so obtained. It is also possible to conduct the reaction in one single step without isolating any intermediate.

In case practical reasor suggest to adopt a two-steps process (as, for instance, in the case of cyclohexanone, whose low boiling point would require the use of sealed vessels), it is possible to obtain different intermediates according to the media (acidic, alkaline or neutral) in which the first step takes place. Hydroxylactone (III) (which is obtained by boiling cyclohexanone and pyruvic acid in a solution containing acetic acid and hydrochloric acid; hydroxy ester $IV_a$ ($R'=C_2H_5$)(which is obtained from ethyl pyruvate and cyclohexanone without condensing agents); hydroxy acid $V_a$ ($R'=H$) (which is obtained from cyclohexanone and sodium pyruvate in water-alcohol solution) and the unsaturated lactone $VI_a$ (which is obtained by dehydration of III) are thus already described in literature (M. Prasad Bull. Soc.Chim. Fr., (1967) 1379-1391)

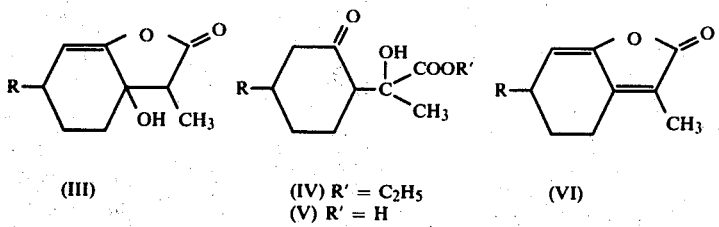

(III)     (IV) R' = C$_2$H$_5$     (VI)
          (V) R' = H

Similar products, not described in literature, are obtained under analogous conditions starting from 3-alkyl substituted cyclohexaones. In this case the condensation takes place in position 6 (and not 2) of the cyclohexanone, as shown by the spectrophotometric characteristics of such intermediates and by the nature of the products which are obtained by subsequent aromatization by further heating between 200 and 250° for some hours in the presence of acids (NCl, HBr, polyphosphoric acid, etc.) or of salts of organic bases with strong acids (pyridine hydrochloride, quinoline hydrochloride, isoquinoline hydrochloride, triethylamine hydrochloride, picoline hydrochloride or mixtures of hydrochlorides of commercial pyridine bases) either lactones of type III and VI, chetoacids and chetoesters of type IV and V give the corresponding hydratropic acids with almost quantitative yields, In the industrial practice, reaction mixtures containing derivatives of type III, IV, V and VI can also be used with very good yields. When the boiling point of the chosen cyclohexanone allows it, the reaction can be effected in one single step. So, 3-isobutyl-cyclohexanone and ethyl pyruvate, mixed with a suitable acidic condensing agent (hydrochloric acid, pyridine hydrochloride, polyphosphoric acid) give, after some hours' heating at 230°, p.isobutylhydratropic acid.

Hydratropic acid and its p. alkyl analogues can be used in human medicine or in the veterinary field, as agrochemicals or as intermediates in the synthesis of organic substances.

The following examples, which are not limitative for the invention, are reported:

EXAMPLES

EXAMPLE 1—Hydratropic acid

A mixture containing 5 g of ethyl α-(2- cyclohexanone) lactate (K. W. Rosemund and coll.—Arch.Pharm. 287 441 (1954)) and 15 g of pyridine hydrochloride is heated for 4-5 hours at 220°. It is then poured into 100 ml of water and the oil which separates is extracted with ether. The residue which is obtained by removing the solvent, is distilled; b.p. 150°-2° (18 mm Hg). NMR, IR and UV spectra are identical to those obtained with an authentic sample. Analogously, hydratropic acid is obtained in the same conditions from α-(2-cyclohexanone)-lactic acid (M. Prasad—1967). Analogously, the hydratropic acid is obtained by heating, for the same time, a mixture formed by 3 portions in weight of pyridine hydrochloride and 1 portion of 3-methyl- 2,4,5,6-tetrahydro-benzo[b]furan-2-one (m. Prasad—1967).

Analogously hydratropic acid is obtained by heating, for the same time, a mixture formed by 3 portions in weight of conc. HCl and 4-hydroxy-2-methyl-3,4-tetramethylene-butenolide (M. Prasad—1967).

EXAMPLE 2—p.isobutyl-hydratropic acid obtained from ethyl pyruvate and 3-isobutylcyclohexanone without separating the intermediates.

A mixture containing equimolecular quantities of ethyl pyruvate and 3-isobutyl-cyclohexanone is heated at 150° for 14 hours. 5 portions in weight of pyridine hydrochloride are added to the viscous oil which is obtained and the mixture is heated for 4–5 hours under reflux (externa bath at 230° ). The mixture is cooled, treated with water, filtered and the solid obtained is crystallized from petrol ether. m.p. 73°–74° also in mixture with an authentic sample (B.P. 971.900). Yield: 63%.

EXAMPLE 3—ethyl α-[2-(5-isobutyl)-cyclohexanone] lactate

The viscous oil which is obtained in Example 2 before the treatment with pyridine hydrochloride is distilled. After some heads formed by a mixture of 3-isobutyl-cyclohexanone and ethyl pyruvate a colourless oil is obtained. b.p. 142°–4° (0.4 mm Hg). Yield: 72%. Analysis: for $C_{15}H_{26}O_4$: Found: C%, 66.39; H%, 9.36. Caled: C%, 66.63; H%, 9,69.

I.R. (5% in $CCl_4$) $\gamma_{OH}=3540$ cm$^{-1}$; $\gamma_{C=(ester)}1730$ cm$^{-1}$; $\gamma_{C=O\ (chetone)}1710$ cm$^{-1}$.

EXAMPLE 4—p.isobutyl-hydratroic acid obtained from ethyl α-[2-(5-isobutyl)-cyclohexanone] lactate 1 portion of ethyl α-[2-(5-isobutyl)-cyclohexanone] lactate and 5 portions of pyridine hydrochloride are refluxed (external bath at 230° ) for 4–5 hours. The solution is cooled, treated with water, filtered and re-crystallized frm petrol ether. m.p. 72°–73° also in mixture with an authentic sample. Yield: >85%.

EXAMPLE 5—6-isobutyl-3-methyl-2,4,5,6-tetrahydro-benzo[b]-furan-2-one

A mixture containing 31 g. of 3-isobutyl-cyclohexanone, 17.6 g. of pyruvic acid, 90 ml of glacial acetic acid and 90 ml of conc. HCl is kept refluxing for 4 hours under stirring. The solution is cooled, diluted with 100 ml of water, extracted with ether. The ethereal extracts are washed with a saturated solution of sodium bicarbonate, then with 2N NaOH and with water. After drying over sodium sulfate and removing the solvent, the residue (31.3 g) is distilled. A first fraction, collected at b.p. 80°–83° (0.3 mm Hg) is formed by 3-isobutyl-cyclohexanone, and a second fraction collected at b.p. 164°–168° (0.3 mm Hg) is formed by 6-isobutyl-3-methyl,2,4,5,6-tetrahydro-benzo[b]-furan-2-one. Yield: 52% of a viscous oil. Analysis: for $C_{13}H_{18}O_2$: Found: C%, 74.90; H%, 8.91. Calcd.: 75.69; H% , 8.80.

NMR spectrum ($CCl_4$, TMS) $\delta5,5$, doublet J=4 cps (1H), (—C$\underline{H}$=C<), $\delta1,73$, singlet, 3H ($CH_3$—).

IR spectrum ($CCl_4$) $\gamma_{C=O}1775$ cm$^{-1}$.

EXAMPLE 6—p. isobutyl-hydratropic acid obtained from 6-isobutyl-3-methyl-2,4,5,6-tetrahydro-benzo[b]furan-2-one 10 g. of the former product and 50 g. of a mixture of hydrochlorides, obtained from a commercial mixtures of pyridine bases, are refluxed for 4–5 hours (external bath at 230° ). The solution is cooled, treated with water, filtered, crystallized from petrol ether. Yield:>80% m.p. 73–74°, also in mixture with an authentic sample.

EXAMPLE 7—p.isobutyl-hydratropic acid obtained from the reaction mixture between 3-isobutyl-cyclohexanone and sodium pyruvate 71.5 g. of sodium pyruvate, 50 g. of 3-isobutyl-cyclohexanone, 200 ml of glacial acetic acid, 300 ml of concentrated hydrochloric acid are refluxed under stirring for 8 hours. The solution is cooled, diluted with 200 ml of water, the upper oily phase is extracted with benzene. After removing the solvent 330 g. of pyridine hydrochloride are added to the residue.

The mixture is refluxed for 4–5hours under stirring (external bath at 230° ). The solution is cooled, diluted with 1,2 litres of water and extracted with 2×300 ml of chloroform. The chloroform extracts are combined and concentrated to dryness and the residue is dissolved in a water bath in 60 ml of 20% NaOH. After cooling, the sodium salt of p.isobutyl-hydratropic acid solidifies and is crushed with 600 ml of acetone. After a short rest in ice box, the solution is filtered, washed with acetone and dried at 50°. Yield: 67%. The sodium salt thus obtained is dissolved in 10 portions of water and strongly acidified with HCl 1:1. p. isobutyl-hydratropic acid, in very small particles, precipitates and is separated by filtration, washed several times with water and dried at 50° till a constant weight is obtained. m.p. 72°–74° also in mixture with an authentic sample.

EXAMPLE 8—p.isopropyl-hydratropic acid obtained from 3-isopropyl-cyclohexanone and tartaric acid A mixture containing 1 portion of 3-isopropyl-cyclohexanone, 3 portions of tartaric acid and 15 portions of α-picoline hydrochloride is refluxed for 5 hours. It is then cooled, poured into water, extracted with ether. The ethereal solution is re-extracted with 1N NaOH. The aqueous solution is acidified and the oil which precipitates is re-extracted with ether. The residue obtained after removal of the solvent is purified by means of sodium salt, as described in Example 7. After re-crystallization from petrol ether m.p. is 67°–68°.

By one or more of the processes described in the above examples, it has been possible to prepare:
p.methyl-hydratropic acid—b.p. 165°–8° (18 mm Hg)
p.n.butyl-hydratropic acid—b.p. 145° (0.3 mm Hg)
p.t.butyl-hydratropic acid—m.p. 100°–2°.

I claim:

1. A process for the production of hydratropic acids of the formula:

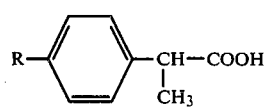

I where R is H or lower alkyl of 1–4 carbon atoms, which comprises aromatizing the condensation product of a cyclohexanone of the formula:

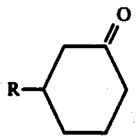

and pyruvic acid or an ester thereof of the formula:

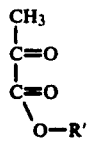

VII where R' is selected from the group consisting of hydrogen, alkali, alkaline earth metals, and alkyl groups of 1 to 4 carbon atoms, said aromatization being effected by heating said condensation product for a period of about 4 to 5 hours to a temperature in the range of 200°–250° C. in the presence of salts of organic bases with strong acids wherein said organic base is selected from the group consisting of pyridine, quinoline, isoquinoline, picoline or triethylamine.

2. The process according to claim 1, wherein said condensation is in acid media and an intermediate hydroxy-lactone is formed.

3. The process according to claim 1, wherein said condensation is in alkaline media and an intermediate hydroxy ester and/or hydroxy acid is formed.

4. The process according to claim 1, wherein said acid condensation is in neutral media and an intermediate unsaturated lactone is formed.

5. The process according to claim 1, wherein ethyl α-(2-cyclohexanone) lactate is heated at 220°–230° C. for 4–5 hours to give hydratropic acid.

6. The process according to claim 1, wherein 4-hydroxyl-2-methyl-3,4-tetramethylene-butenolide in heated at 220°–230° C. to give hydratropic acid.

7. The process according to claim 1, wherein 3-methyl-2,4,5,6-tetrahydro[b]-furan-2-one is heated at 220°–230° C. to give hydratropic acid.

8. The process according to claim 1, by which 3-isobutyl-cyclohexanone and ethyl pyruvate are condensed to give ethyl α-[2-(5-isobutyl)-cyclohexanone] lactate and without separation of the resultant condensation product it is aromatized to p-isobutyl hydratropic acid.

9. The process according to claim 8, by which 3-isobutyl-cyclohexanone and ethyl pyruvate are condensed without solvent and the condensate formed is heated at 220°–230° C. to give p-isobutyl-hydratropic acid.

10. The process according to claim 1, by which ethyl α-[2-(5-isobutyl)-cyclohexanone] ethyl lactate is heated with pyridine hydrochloride at 220°–230° C. to give p-isobutylhydratropic acid.

11. The process according to claim 1, wherein 3-isobutyl-cyclohexanone and pyruvic acid are heated in an HCl and acetic acid solution to give 6-isobutyl-3-methyl-2,4,5,6-tetrahydro-benzo[b]-furan-2-one and this product is heated for 4 to 5 hours with pyridine hydrochloride to give p-isobutylhydratropic acid.

12. The process according to claim 1, wherein 3-isobutyl-cyclohexanone and sodium pyruvate are heated in a HCl and acetic acid solution to give a mixture of condensation products and said condensation products are heated for 4 to 5 hours with pyridine hydrochloride to give p-isobutylhydratropic acid.

13. The process according to claim 1, wherein the 3-alkyl-cyclohexanone is heated at 220°–230° C. with tartaric acid in the presence of salts of an organic base with strong acids to give a p-alkyl hydratropic acid.

* * * * *